United States Patent
Touchet et al.

(10) Patent No.: US 12,336,745 B2
(45) Date of Patent: Jun. 24, 2025

(54) SEMI-RIGID DEVICE FOR ORTHOPEDIC FIXATION

(71) Applicant: Trilliant Surgical LLC, Houston, TX (US)

(72) Inventors: Tyler Joseph Touchet, Cypress, TX (US); Jon Olson, Houston, TX (US)

(73) Assignee: Trilliant Surgical LLC, Houston, TX (US)

( * ) Notice: Subject to any disclaimer, the term of this patent is extended or adjusted under 35 U.S.C. 154(b) by 491 days.

(21) Appl. No.: 17/739,695

(22) Filed: May 9, 2022

(65) Prior Publication Data
US 2022/0354557 A1    Nov. 10, 2022

Related U.S. Application Data

(60) Provisional application No. 63/186,425, filed on May 10, 2021.

(51) Int. Cl.
*A61B 17/86* (2006.01)
*A61B 17/04* (2006.01)

(52) U.S. Cl.
CPC ...... *A61B 17/8635* (2013.01); *A61B 17/8605* (2013.01); *A61B 2017/0443* (2013.01); *A61B 2017/0445* (2013.01)

(58) Field of Classification Search
CPC ............ A61B 17/8635; A61B 17/8625; A61B 17/866; A61B 17/8685; A61B 17/869
See application file for complete search history.

(56) References Cited

U.S. PATENT DOCUMENTS

| | | | |
|---|---|---|---|
| 4,959,064 A | 9/1990 | Engelhardt | |
| 7,625,395 B2 * | 12/2009 | Muckter | A61B 17/866 606/300 |
| 2002/0198527 A1 | 12/2002 | Muckter | |
| 2003/0202861 A1 * | 10/2003 | Nelson | F16B 35/041 411/487 |
| 2016/0038201 A1 * | 2/2016 | Cummings | A61B 17/8875 606/304 |
| 2020/0138485 A1 * | 5/2020 | Kuwamura | A61B 17/8685 |
| 2020/0146735 A1 | 5/2020 | Pepper et al. | |

OTHER PUBLICATIONS

International Search Report from PCT/US2022028325 dated Sep. 19, 2022.

* cited by examiner

*Primary Examiner* — Olivia C Chang
(74) *Attorney, Agent, or Firm* — Veros Legal Solutions, LLP

(57) ABSTRACT

A semi-rigid, fixation device includes a rigid anchor portion configured to be directly rotated and driven distally into a first bone or bone portion of a patient. The device includes a rigid cap portion configured to be held in tension against at least one of a bone plate and a second bone or bone portion of the patient and indirectly rotated under torque provided by the anchor portion. The device includes a flexible member including a plurality of woven stands and having a fixed length between first and second ends, which are fixedly respectively coupled to the anchor portion and cap portion, such that a torque provided by the direct rotation of the anchor portion is transferred through the flexible member to the cap portion when the flexible member is held in at least a first amount of longitudinal tension. Methods of use and manufacture are also provided.

23 Claims, 11 Drawing Sheets

SEMI-RIGID DEVICE FOR ORTHOPEDIC FIXATION

CROSS-REFERENCE TO RELATED APPLICATIONS

This application claims the benefit of U.S. Provisional Patent Application No. 63/186,425, filed May 10, 2021, which is hereby incorporated by reference herein in its entirety.

FIELD OF THE DISCLOSURE

The disclosure relates to semi-rigid devices for orthopedic fixation. More specifically, the disclosure relates to semi-rigid fixation devices having two substantially rigid members coupled to one another via a flexible member, the flexible member coupled to a respective one of the substantially rigid members at each end. Methods of using and/or manufacturing such semi-rigid fixation devices are likewise provided.

BACKGROUND

In the field of orthopedic fixation, various devices and methods have been used in the prior art for bone realignment, fixation of the bones or bone portions, and ligament reconstruction repair in order to correct for various orthopedic conditions, such as hallux valgus, tarsometatarsal sprains, ankle ligament reconstruction, and ligament repair.

A syndesmosis is a type of joint. More specifically, a syndesmosis is a movable articulation where contiguous bony surfaces are united by an interosseous ligament. An example is the inferior tibiofibular articulation of the ankle. This syndesmosis is made up of the anterior tibiofibular ligament, the interosseous ligament, and the posterior-fibular ligaments. Following trauma to the ankle, such as an ankle fracture, the syndesmotic joint can become unstable and painful.

Syndesmosis injury can also occur without fracture, such as with a severe ankle sprain. An example of this type of syndesmosis injury is torn ligaments without any bone fracture. Surgery may be needed to stabilize the syndesmotic joint to allow these ligaments to properly heal.

Various injuries include separation of soft tissue from one or more bones and/or separation of bones from normally anatomical correct positioning. Maintaining the bones in the correct anatomical positions during healing is important to provide proper soft tissue reattachment and proper bone healing.

The current standard of care involves fixing the fibula to the tibia during the soft tissue healing process with one or two screws that are continuously rigid along their lengths of extent. Because these screws can inhibit normal joint motion, the screws are typically removed after the ligament injury is healed. Typically, syndesmosis repair systems and methods rely on such continuously rigid screws for coupling the tibia and the fibular and replacing the syndesmosis. These continuously rigid screws inhibit normal movement and articulation of the bones, for example, the tibia and fibula, and further limit one or more corresponding joints.

Accordingly, current solutions fail to provide or maintain the natural flexibility and lateral movement of the bones, required for treating injuries such as but not limited to syndesmosis. Therefore, there is a need in the art for improved methods and devices for treating injuries such as but not limited to syndesmosis, including ankle syndesmosis injuries.

It should be noted that this Background is not intended to be an aid in determining the scope of the claimed subject matter nor be viewed as limiting the claimed subject matter to implementations that solve any or all of the disadvantages or problems presented above. The discussion of any technology, documents, or references in this Background section should not be interpreted as an admission that the material described is prior art to any of the subject matter claimed herein.

SUMMARY

It is understood that various configurations of the subject technology will become apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

In some embodiments, a semi-rigid fixation device for orthopedic fixation is provided. The device includes a rigid anchor portion configured to be directly rotated and driven distally into a first bone or bone portion of a patient. The device includes a rigid cap portion configured to be held in tension against at least one of a bone plate and a second bone or bone portion of the patient and indirectly rotated under a torque provided by the rigid anchor portion. The device includes a flexible member comprising a plurality of woven stands. The flexible member has a fixed length between a first end and a second end. The first end is fixedly coupled to the rigid anchor portion. The second end is fixedly coupled to the rigid cap portion such that a torque provided by the direct rotation of the rigid anchor portion is transferred through the flexible member to the rigid cap when the flexible member is held in at least a first amount of longitudinal tension.

In some other embodiments, a method of using a semi-rigid fixation device for orthopedic fixation of a bone is provided. The method includes directly rotating a rigid anchor portion of a fixation device, thereby driving the rigid anchor portion distally into a first bone or bone portion of a patient. The rigid anchor portion is fixedly coupled to a first end of a flexible member that includes a plurality of woven strands and has a fixed length. A second end of the flexible member is fixedly coupled to a rigid cap portion. The method includes causing the rigid cap portion to be indirectly rotated under a torque provided by the rigid anchor portion and transferred through the flexible member when the rigid cap portion is held in at least a first amount of longitudinal tension against at least one of a bone plate and a second bone or bone portion of the patient.

In yet other embodiments, a method of manufacturing a semi-rigid fixation device for orthopedic fixation of a bone is provided. The method includes providing a flexible member that includes a plurality of woven stands and has a fixed length. The method includes fixedly coupling a first end of the flexible member to a rigid anchor portion that is configured to be directly rotated and driven distally into a first bone or bone portion of a patient. The method includes fixedly coupling a second end of the flexible member to a rigid cap portion that is configured to be indirectly rotated under a torque provided by the rigid anchor portion and transferred through the flexible member when the rigid cap portion is held in at least a first amount of longitudinal tension against at least one of a bone plate and a second bone or bone portion of the patient.

BRIEF DESCRIPTION OF THE DRAWINGS

Various embodiments are discussed in detail in conjunction with the Figures described below, with an emphasis on highlighting the advantageous features. These embodiments are for illustrative purposes only and any scale that may be illustrated therein does not limit the scope of the technology disclosed. These drawings include the following figures, in which like numerals indicate like parts.

DETAILED DESCRIPTION

Figure 1:
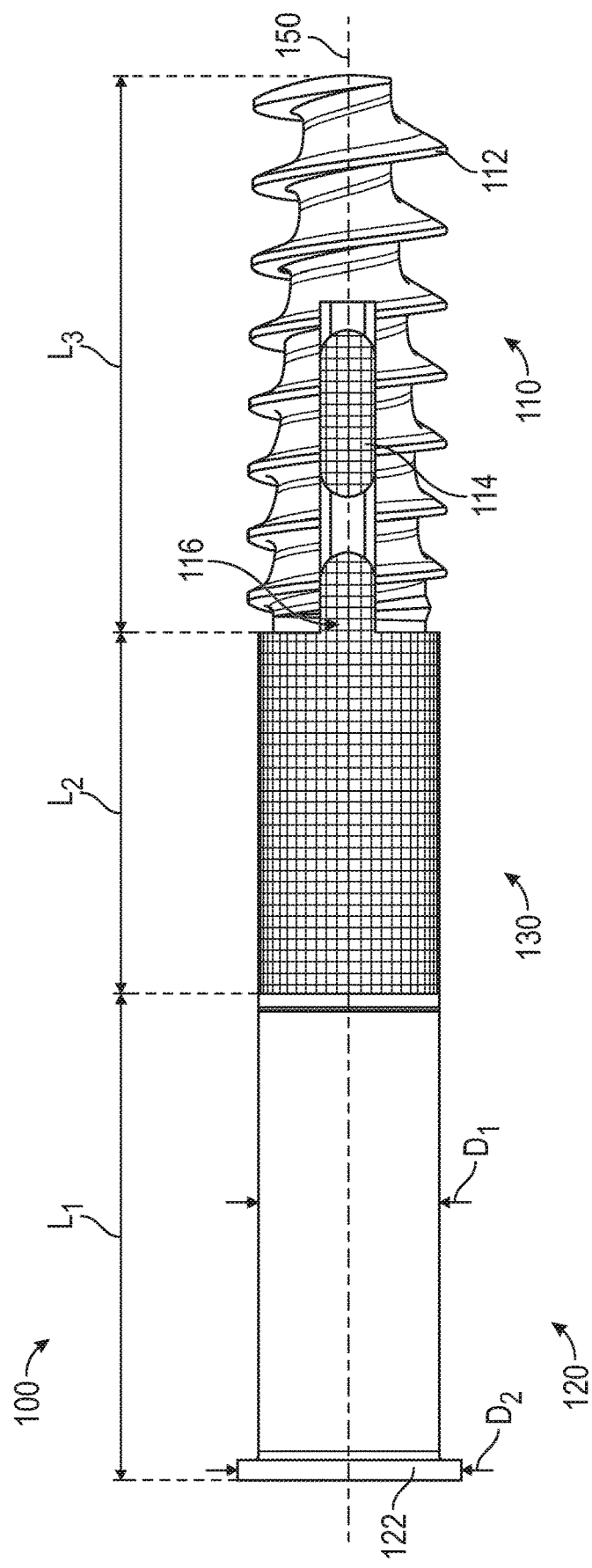
FIG. 1 is a side view of a fixation device, according to some example embodiments.

The following description and examples illustrate some exemplary implementations, embodiments, and arrangements in detail. Those of skill in the art will recognize that there are numerous variations and modifications of such exemplary implementations, embodiments, and arrangements that are encompassed by its scope. Accordingly, the description of a certain example embodiment should not be deemed to limit the scope of the present disclosure.

Implementations of the technology described herein are directed generally to a semi-rigid device for orthopedic fixation.

As used herein, the terms "proximal" and "distal" denote a relative location or orientation of a particular feature with respect to other potential locations and/or orientations for that feature with respect to some reference. Often this reference may be with respect to a direction of extension or with respect to a practitioner. For example, the proximal end of fixation devices described herein corresponds to the end nearest the cap portion and the distal end corresponds to the opposite end, along the longitudinal length of extension 150 (see, e.g., FIG. 1). The terms proximal and distal may also reference the relative side, end or surface of a particular feature of with the same correspondence to and along the longitudinal length of extension 150.

The disclosure relates to a fixed-length flexible fixation device that does not rely on additional tensioning steps, sutures, laser-cut, or flexible metallic components. The device can be used where semi-rigid fixation is needed (i.e., syndesmotic repair). In some exemplary implementations, embodiments, and arrangements two substantially cylindrical components may be attached inline with a third intermediate component that provides anchored fixation to bone and/or soft tissue. In some embodiments, tension and degree of fixation are determined by the insertion depth of the third component. Such exemplary implementations, embodiments, and arrangements provide the benefits of both a solid fixation for tension or axial load while providing movement or translation laterally. This is especially important in the primary target application of syndesmotic joint repair. The syndesmotic joint is an effective joint that stabilizes the motion between the fibula and tibia at the interface with the talus. Mobility is maintained by the slight motion allowed.

There are several problems solved by these exemplary implementations, embodiments, and arrangements. First, they allow for fixation/stabilization of damaged ligaments, tendons, or bone. Second, due to the second component's tubular nature, the problems in current devices such as "suture sawing" (motion of a small or thin section of suture over time with motion abrades the surrounding bone) or loss of tension are reduced if not eliminated. In addition, the second component is comprised of a woven textile, further reducing the susceptibility to creep (loss of tension). Further benefits are simplified adjustment to the amount of tension or stabilization desired. In a traditional suture approach often times two hands are required to pull axially while a technician holds or stabilizes the joint or in connection with a large bone clamp. In the preferred embodiment, a one-handed application can be performed with a driver handle while using the other hand to manually reduce/gauge the fixation.

Figure 2:
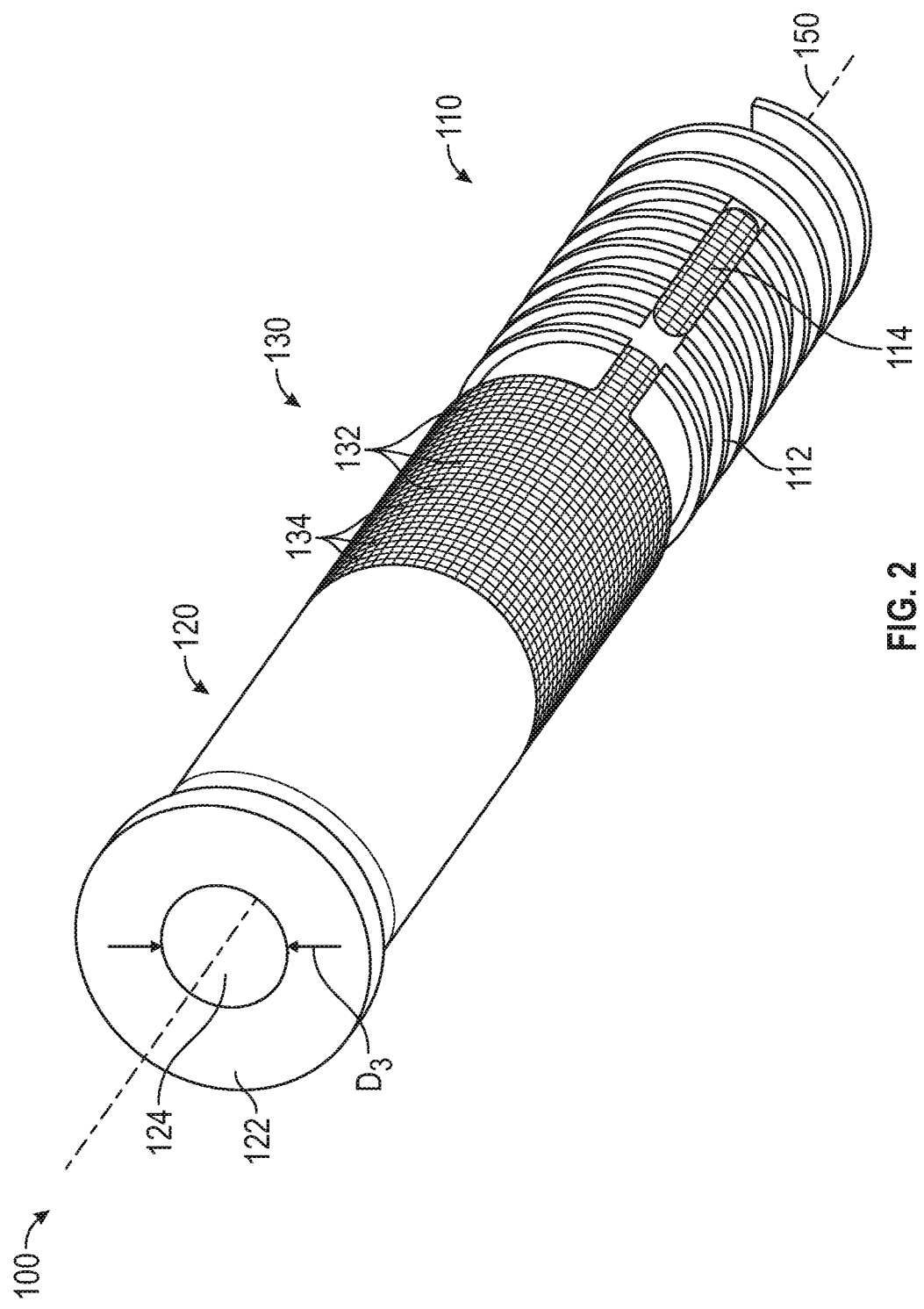
FIG. 2 is a perspective view of the fixation device of FIG. 1.
Figure 3:
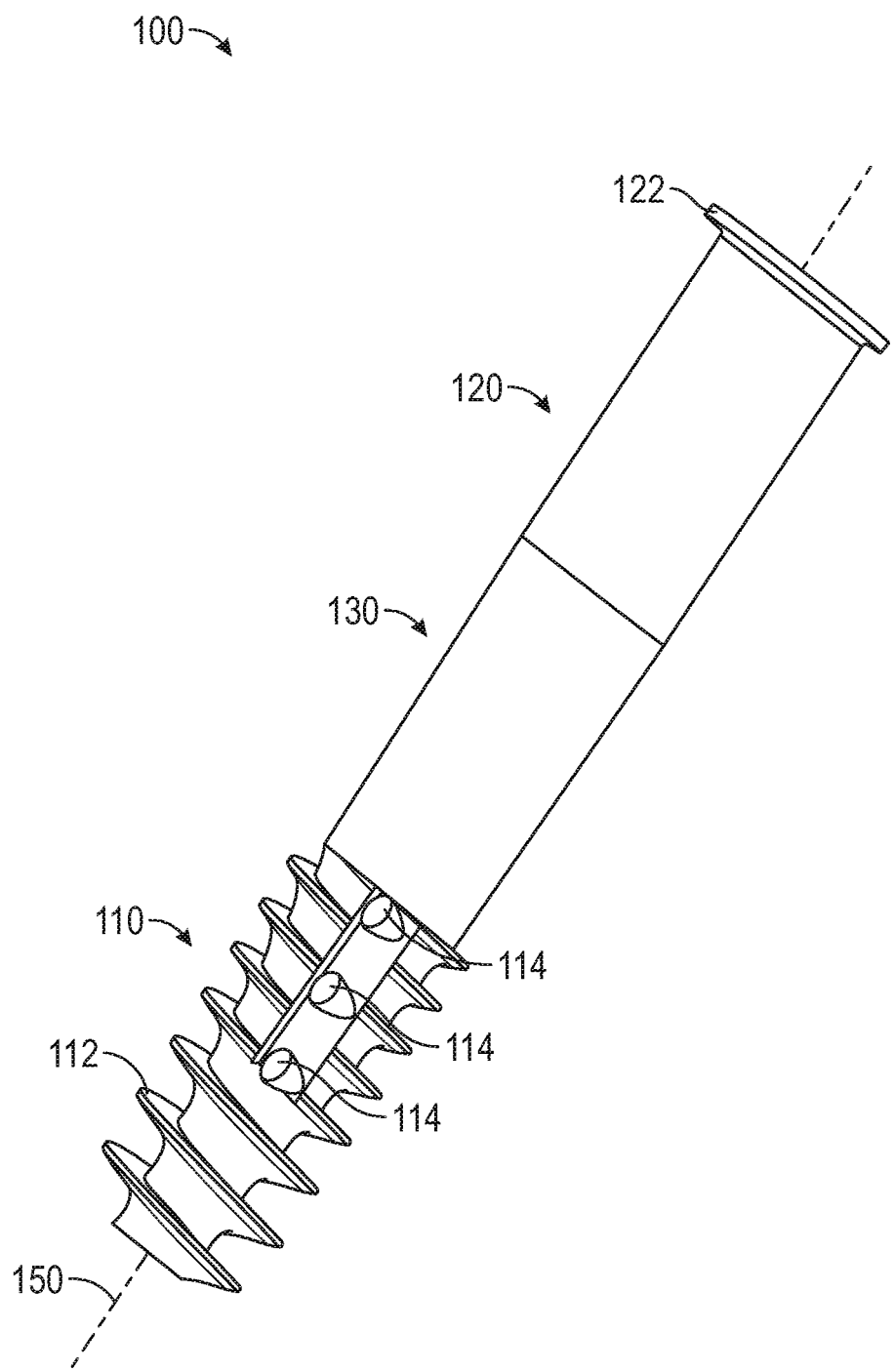
FIG. 3 is a side view of a fixation device, according to some example embodiments.

FIGS. 1 and 3 illustrate side views, while FIG. 2 illustrates a perspective view of a fixation device 100, according to some example embodiments. Fixation device 100 comprises an anchor portion 110, a cap portion 120, and a flexible member 130. In some embodiments, anchor portion 110 and cap portion 120 are each rigid. As shown, cap portion 120, flexible portion 130, and anchor portion 110 each have a respective length $L_1$, $L_2$ and $L_3$. In some embodiments, one or more of these lengths may depend on the particular application. For example, and not limitation, the length $L_1$ of cap portion 120 may be related to, slightly longer than, slightly shorter than or substantially equal to a width of a fibula (e.g., fibula 910 in FIG. 9) of the patient in which fixation device 100 is to be implanted. In some such examples, a length $L_2$ of flexible member 130 may be chosen based on a typical anatomically correct spacing or actual anatomically correct spacing between a fibula and tibia of a patient in which fixation device 100 is to be implanted. Such a length $L_2$ of flexible member 130 may also take into consideration the torsional rigidity qualities of varying woven or total lengths of flexible member 130. And anchor portion 110 may have a length $L_3$ determined with a capacity for distal advancement and tensioning of flexible member 130 as a result of such distal advancement relative to cap portion 120, as will be described in more detail below. In some embodiments, anchor portion 110, flexible member 130, and cap portion 120 are coupled in-line with one another such that a longitudinal axis of extension 150 through a center of fixation device 100 is coincident with individual longitudinal axes through respective centers of each of anchor portion 110, flexible member 130, and cap portion 120. Such axial alignment through each component's center may contribute to one or more advantages of any fixation device disclosed herein, as will be discussed in more detail below.

Anchor portion 110 and/or cap portion 120 may comprise any suitable biocompatible metal or polymer such as Ti-6Al-4V, PEEK, polyester, polyamide, polyurethane, polyethylene, ultra-high molecular weight polyethylene (UHMWPE) or combinations thereof.

Anchor portion 110 comprises a distal end configured to be driven or otherwise inserted or into bone of a patient, and a proximal end configured to receive a first end of flexible member 130. As illustrated, anchor portion 110 tapers from its proximal end to its distal end. Accordingly, anchor portion 110 may have a substantially conical form that tapers linearly and/or a substantially convex and/or concave conical shape that tapers non-linearly. As illustrated in FIG. 1, anchor portion 110 may comprise threads 112 configured to bite into the bone of the patient and, thereby contribute to fixation of anchor 110 therein. However, the present disclosure is not so limited and any other suitable method of anchoring is also contemplated. For example, one or more blades or hooks 612 may be substituted for a portion (or all) of threads 112 (see, e.g., FIG. 6). Accordingly, anchor portion 110 contributes to a fixation solution, at least in part, by simultaneously providing a fixation component, a tension component, and a torque component to fixation device 100.

The proximal end of anchor portion 110 comprises an aperture 116 configured to receive a tool that is configured to impart a torque directly to anchor portion 110. For example, a shape of at least a distal portion of aperture 116 may be complementary to a shape of a terminal end of such a tool, thereby allowing the tool to be releasably engaged with anchor portion 110, through cap portion 120 and flexible member 130. In some embodiments, anchor portion 110 may comprise one or more holes or apertures 114 bored through its side and into aperture 116. Holes 114 may be utilized to tie or otherwise fix an end or immediately adjacent end portion of flexible member 130 to anchor portion 110.

Fixation devices utilizing alternatively-configured anchor portions are also contemplated. For example, see FIG. 6 and related discussion below.

Cap portion 120 may have a substantially cylindrical form. Cap portion comprises a distal end configured to receive a second end of flexible member 130. In some embodiments, a proximal end of cap portion 120 comprises a lip or rim 122. For example, lip or rim 122 may have a diameter $D_2$ that is greater than a diameter $D_1$ of immediately adjacent, joining surfaces of cap portion 120. In some embodiments, D1 may be approximately 4 millimeters (mm). However, the present disclosure is not so limited and $D_1$ may have any suitable value.

In some embodiments, a distal surface of rim 122 may be substantially perpendicular or normal to the adjoining, adjacent surface of cap portion 120. In some other embodiments, the distal surface of rim 122 may intersect the adjoining, adjacent surface of cap portion 120 at an angle (e.g., be beveled) or may curve to provide a smooth transition from the distal surface of rim 122 to the adjoining, adjacent surface of cap portion 120. At least a portion of the distal surface of rim 122 is configured to abut or directly contact at least one of a bone plate (see, e.g., bone plate 900 in FIG. 9), other rigid body, or a bone of a patient as anchor portion 110 is driven into bone of the patient.

As shown in FIG. 2, an aperture 124 extends entirely through cap portion 120 and has a diameter $D_3$ smaller than the diameter $D_1$ but sufficiently large to allow the terminal end of the tool described in connection with anchor portion 110 to extend completely through cap portion 120, completely through flexible portion 130, and into aperture 116 of anchor portion 110.

The respective ends of flexible portion 130 are fixedly coupled to anchor portion 110 and cap portion 120 such that, as the tool that is disposed through aperture 124 of cap portion and through flexible portion 130 imparts torque directly to anchor portion 110, anchor portion 110 rotates and advances distally into the bone as teeth 112 bite into the bone. This distal advancement of anchor portion 110 imparts a longitudinal tension substantially along axis 150 (see, e.g., FIG. 1) that pulls the distal surface of rim 122 into this bone plate, other rigid body, or bone. The fixed coupling of respective ends of flexible member 130 to cap portion 120 and anchor portion 110, in combination with particular features of flexible member 130 discussed below, allow flexible member 130 to transmit torque from anchor portion 110 to cap portion 120 simultaneous to, and at least partially as a result of, the generation of this axial or longitudinal tension, thereby causing cap portion 120 to rotate through substantially the same angle as anchor portion 110. This feature is made possible, at least in part, by particular aspects of flexible member 130 that allow it to efficiently transmit torque when held in sufficient tension, as will be discussed in more detail below.

An amount of friction between at least the distal surface of rim 122 of cap portion 120 and bone plate 900, other rigid body, and/or bone of the patient is proportional to the coefficient of static or sliding friction therebetween (depending on whether cap portion 120 is stationary or rotating, respectively) and proportional to the magnitude of the axial tension imparted tangent (or normal) to mutually-contacting surfaces thereof. But the amount of torque imparted to cap portion 120, which flexible member 130 transfers from anchor portion 110, depends on the torque imparted by tool on anchor portion 110 to rotate and distally advance anchor portion 110 into the bone. Accordingly, as the distal surface of rim 122 of cap portion 120 is held against bone plate 900, other rigid body, and/or bone of the patient and anchor portion 110 is distally advanced into bone, tension in flexible member 130 increases. This tension increasingly stabilizes flexible member 130, thereby allowing continued efficient transmission of torque from anchor portion 110 to cap portion 120 until cap portion 120 and/or anchor portion 110 are properly implanted in the patient. This maintenance of axial tension in flexible member 130 and the consequent transmission of torque therethrough, directly allows anchor portion 110 and cap portion 120 to rotate together, providing substantial elimination of relative rotation therebetween, as well as elimination of attendant bunching of flexible member 130 that such relative rotation would otherwise cause.

In addition to the embodiments of cap portion 120 and anchor portion 110 illustrated in FIGS. 1-3, the present disclosure also contemplates different geometries for each. For example, a portion of cap portion 120 (or of any other cap portion described herein) may comprise a locking feature or interface configured to releasably lock with the above described the bone plate, other rigid body, and/or bone of the patient. An example of such a locking feature may be one or more grooves and/or protrusions configured to interlock.

Figure 4:
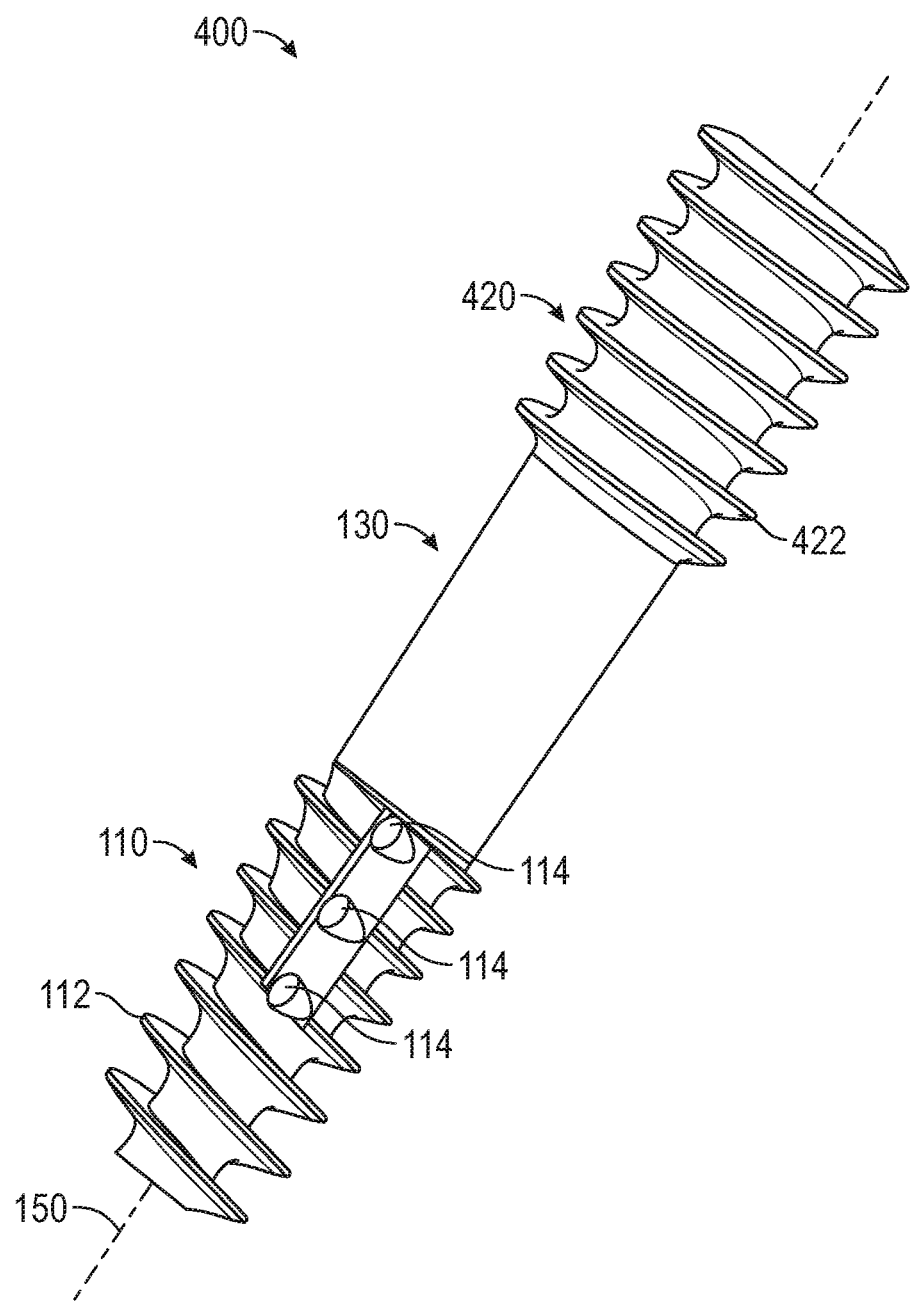
FIG. 4 is a side view of a fixation device, according to some other example embodiments.

As another example, FIG. 4 illustrates a fixation device 400 comprising anchor portion 110 and flexible member 130 as described herein, but substituting cap portion 420 in place of cap portion 120 of FIGS. 1-3. Instead of having a smooth, cylindrical form as with cap portion 120, cap portion 420 comprises threads 422, which may be substantially similar or identical to threads 112 of anchor portion 110. Accordingly, threads 422 are configured to bite into or engage with at least one of bone plate 900, other rigid body, and/or bone of the patient bone as described herein. While not illustrated in FIG. 4, cap 420 may also comprise rim 122, as previously described in connection with FIG. 1, at its proximal end.

Figure 5:
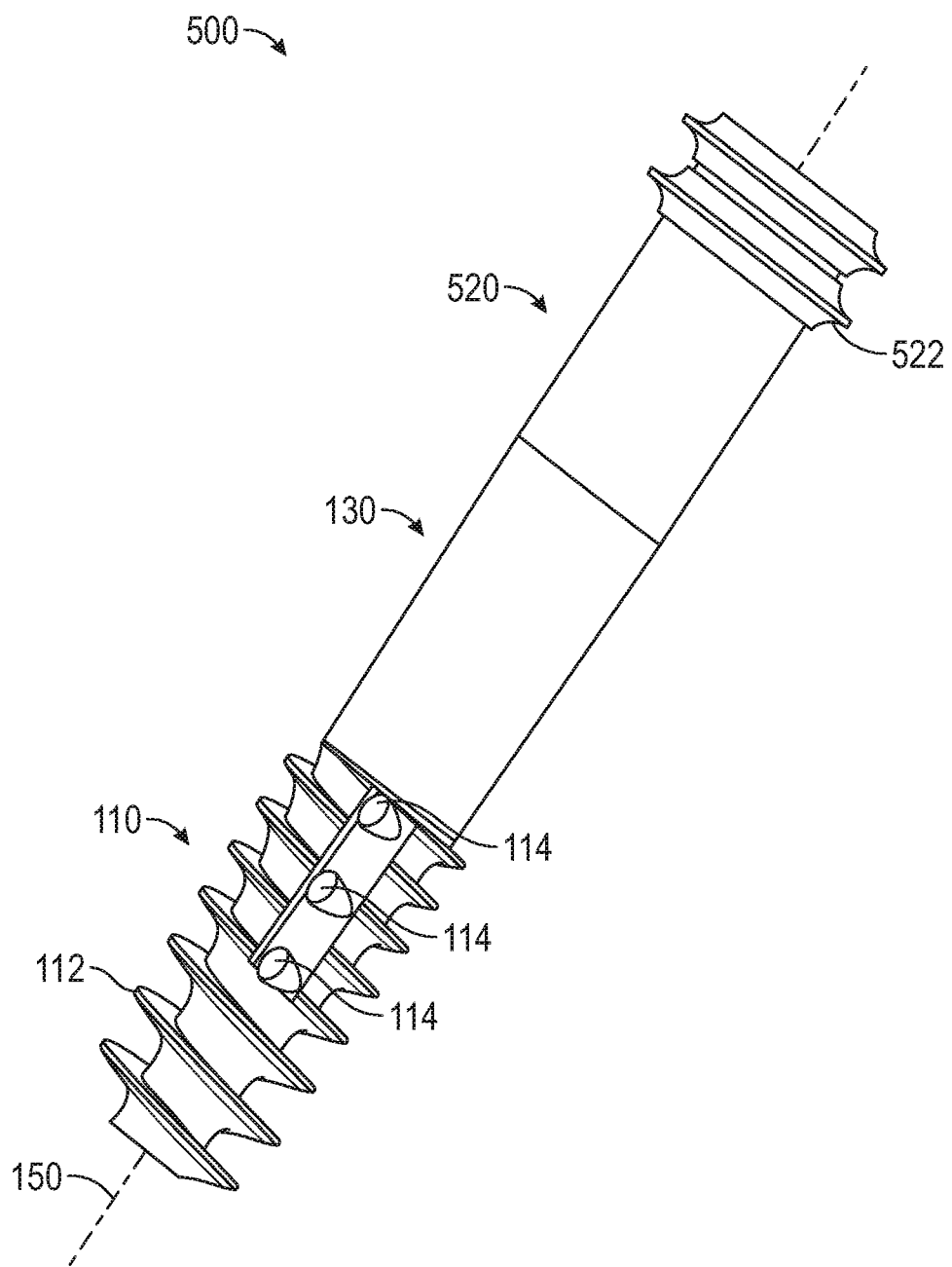
FIG. 5 is a side view of a fixation device, according to yet other example embodiments.

As yet another example, FIG. 5 illustrates a fixation device 500 comprising anchor portion 110 and flexible member 130 as described herein, but substituting cap portion 520 in place of cap 120 of FIGS. 1-3. Instead of or in addition to having a smooth, cylindrical form, cap 420 comprises one or more circumferential or partially-circumferential blades 522 configured to allow friction-fit seating of cap 420 into at least one of the bone plate, other rigid body, and/or bone (e.g., cortical bone) of the patient. In some embodiments, blades 522 are sufficiently flexible to allow sufficient deformation in a first direction or sense as cap portion 520 is rotated and pulled distally into the seated position bone. However, in some such embodiments, blades 522 are formed to resist symmetrical deformation in a second direction or sense that is opposite to the first direction or sense, e.g., having a distal surface that is beveled or sloped with respect to axis 150 and a proximal surface that is substantially perpendicular to axis 150. In some other embodiments, blades 522 are formed to theoretically allow symmetrical deformation in a second direction or sense that is opposite to the first direction or sense, e.g., having substantially symmetrically oriented proximal and distal surfaces, but such that this deformation is resisted by the restricted space in which blades 522 are disposed when cap portion 520 is seated within at least one of bone plate 900, other rigid body, and/or bone of the patient bone as described herein. While not illustrated in FIG. 5, cap 520 may also comprise rim 122, as previously described in connection with FIG. 1, at its proximal end.

Figure 6:
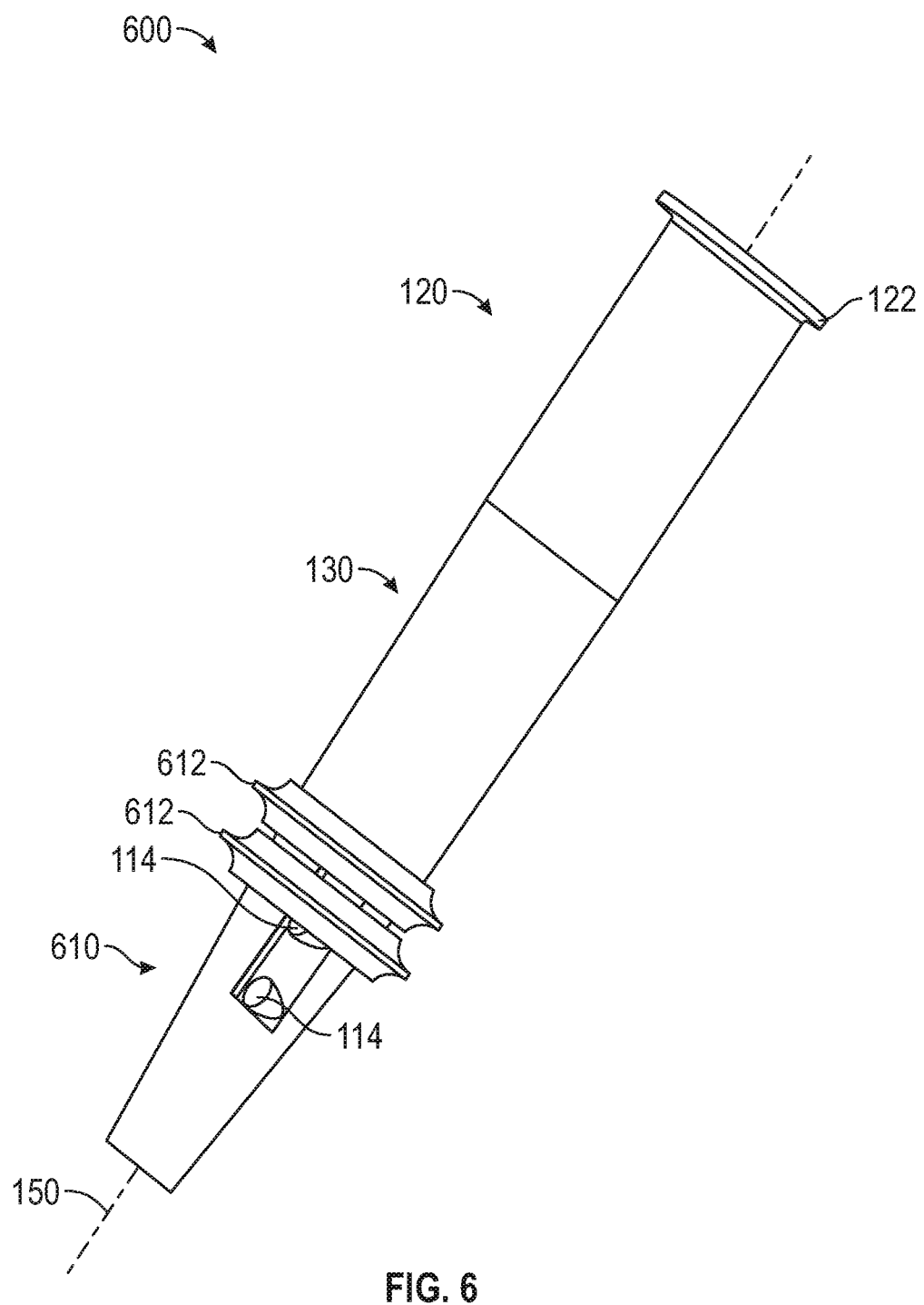
FIG. 6 is a side view of a fixation device, according to yet other example embodiments.

As yet another example, FIG. 6 illustrates a fixation device 600 comprising cap portion 120 and flexible member 130 as described anywhere herein, but substituting anchor portion 610 in place of anchor portion 110. Anchor portion 610 may be substantially as previously described for anchor portion 110 but omitting all (shown) or at least a proximal, medial or distal portion of threads 112 and including one or more blades 612 disposed in place of omitted threads 112. Blades 612 may be substantially the same as blades 512 of FIG. 5, however, being configured to releasably engage or seat against deeper or different bone, being on more distal anchor portion 610 instead of more proximal cap portion 520.

While specific combinations of threaded, bladed, or smooth walled features of an anchor portion or cap portion are illustrated and discussed herein, this disclosure is not so limited and also contemplates any combination of disclosed anchor portion coupled to any other disclosed cap portion by flexible member 130. For example, an anchor portion comprising any combination of a substantially smooth side wall, at least a portion of threads 112, and/or blades 612 may be coupled with a cap portion comprising any combination of a substantially smooth side wall, threads 422, and/or blades 522.

Figure 7:
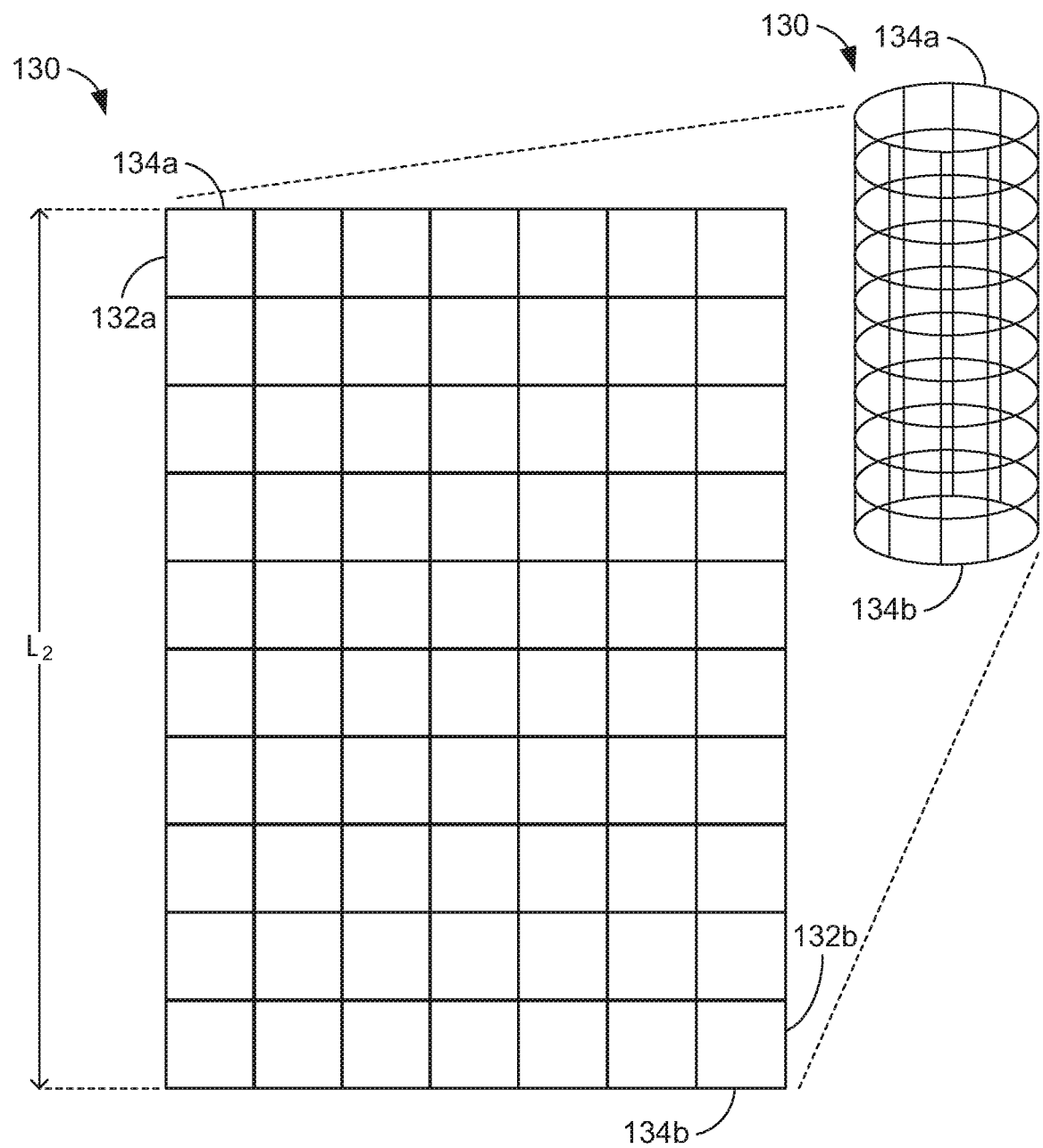
FIG. 7 illustrates a woven tube portion of a fixation device, according to some example embodiments.
Figure 8:
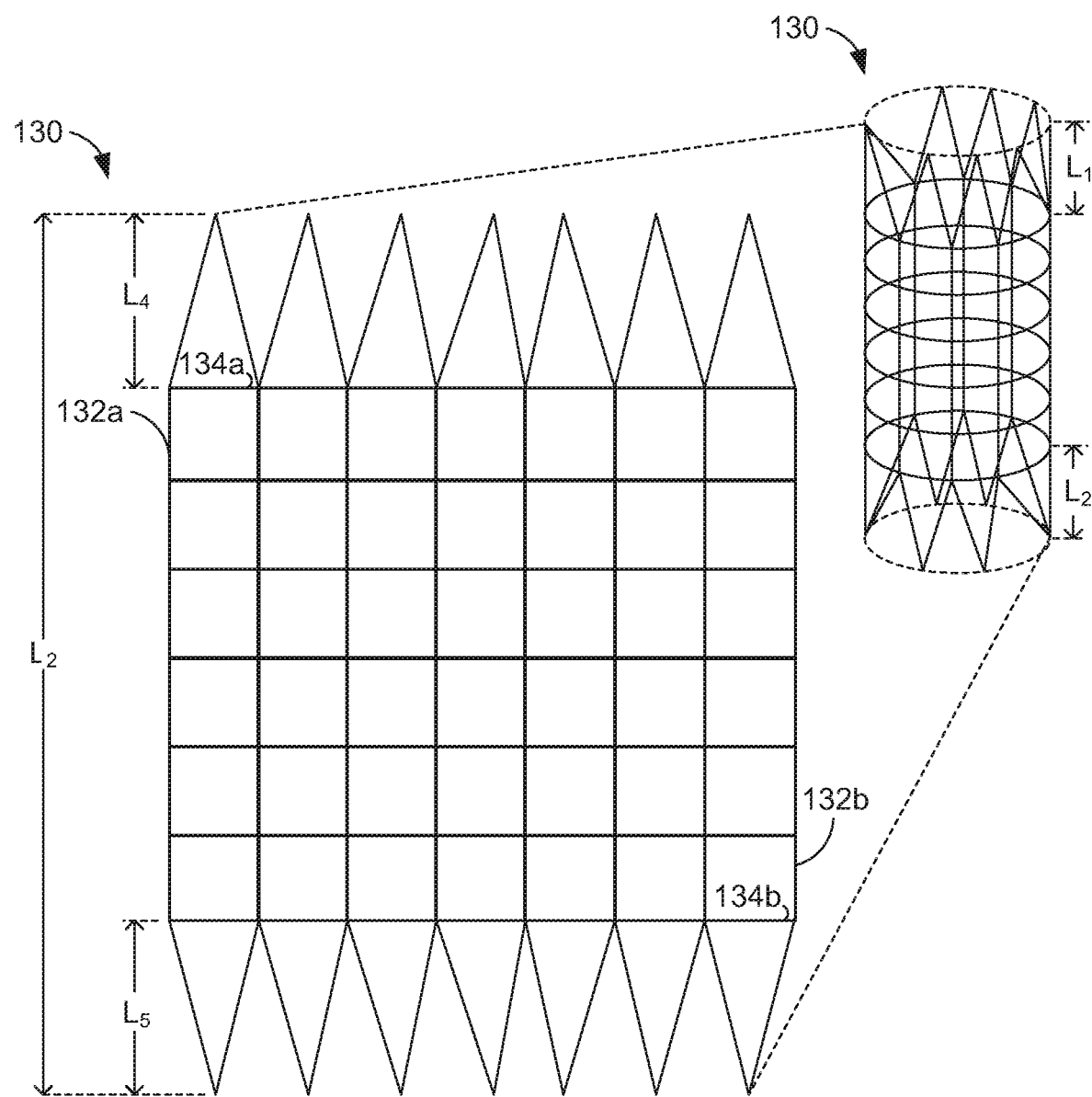
FIG. 8 illustrates a woven tube portion of a fixation device, according to some other example embodiments.

Discussion now turns to flexible member 130. FIGS. 7 and 8 illustrate example embodiments of flexible member 130, as discussed or illustrated anywhere in this disclosure. For the purpose of discussing flexible member 130, several terms are defined below. A "suture" is defined as "a stitch or row of stitches holding together the edges of two or more features," for example, a respective end or immediately adjacent end portion of flexible member 130 and either an anchor portion (e.g., 110, 610) or a cap portion (e.g., 120, 420, 520). A "braid" or "braided" feature is defined as "a length comprising 3 or more interlaced strands, where each interlaced strand follows a substantially same path of extension in common with the entire braid (or braided feature)." A "weave" or "woven" feature is defined as "a plurality of threads passing in a first relative direction interlaced with a different plurality of threads passing in a second relative direction that is substantially different than the first relative direction." For example, interlacing at right angles (90°) generally results in an undistorted weave comprising square or rectangular features formed by the interlaced strands, while interlacing at complementary acute and obtuse angles generally results in an undistorted weave of parallelograms having two of those acute angles and two of those obtuse angles.

Also, note, the terms "first relative direction" and "second relative direction" may be interpreted at each common point of contact or interlacing between two or more threads. For example, two individual threads need not each extend in a single, non-changing direction along its entire length, so long as two such threads extend directly to or from their common point of contact or interlacing in substantially different first and second directions. Accordingly, individual threads may zig-zag between relative directions so long as the threads they interlace with zig-zag in complementary directions.

Although other weaves are contemplated, FIGS. 7 and 8 illustrate a weave substantially comprising the above-described square or rectangular pattern. FIG. 7 shows flexible member 130 comprising threads weaved to form a substantially cylindrical tube, as shown at the upper right of FIG. 7. This cylindrical tube is also visually magnified and flattened as shown at the lower left portion of FIG. 7 to better illustrate the weave. A first plurality of threads 132a, 132b passing in a first relative direction are interlaced with a different plurality of threads 134a, 134b passing in a second relative direction that is substantially different than the first relative direction. In the illustration of FIG. 7, this second relative direction is approximately 90°.

In some embodiments as illustrated in FIG. 7, the weave pattern extends all the way to the respective ends of flexible member 130. In some such embodiments, these respective woven ends are fixedly secured to an anchor portion 110, 610 and to a cap portion 120, 420, 520 in a manner that aids in substantially preventing creep or stress relaxation. For example, the respective woven ends of flexible member 130 may be tied, melted and/or potted to an anchor portion 110, 610 and to a cap portion 120, 420, 520. Alternatively, and/or additionally, the interface between an end or immediately adjacent end portion of flexible member 130 and an anchor portion or a cap portion may comprise a braided or sutured portion, which in some but not all embodiments, is tied into a knot or crimped and press-fit into the anchor portion or cap portion as described anywhere herein.

For example, FIG. 8 shows flexible member 130 substantially as shown in FIG. 7, except that the weave pattern transitions to a sutured pattern, where those strands converge or loop to meet at triangular or sutured ends of flexible member 130. As illustrated, the sutured pattern may extend for a first sub-length $L_4$ of the predetermined length $L_2$ from a first end of flexible member 130. The sutured pattern may also extend for a second sub-length $L_5$ of the predetermined length $L_2$ from a second end of flexible member 130. In some such embodiments, these respective sutured ends are fixedly tied, melted and/or potted to an anchor portion 110, 610 and to a cap portion 120, 420, 520. Alternatively, and/or additionally, the interface between the sutured ends or immediately adjacent end portions of flexible member 130 and an anchor portion or a cap portion may be braided, which in some but not all embodiments, may be tied into a knot or crimped and press-fit into the anchor portion or cap portion as described anywhere herein.

In some embodiments, flexible member 130 has a substantially similar diameter to that of mating ends of the anchor portion and the cap portion. Accordingly, in some but not all embodiments, flexible member 130 has a diameter of approximately 4 mm. In some but not all embodiments, a thickness of flexible member 130 is approximately 0.5 mm. Accordingly, in some but not all such embodiments, the plurality of threads (e.g., 132, 134) from which flexible member 130 is woven may each have diameters of approximately 0.5 mm. However, the present disclosure is not so limited and flexible member 130 and/or its comprised strands may have any suitable thickness(es).

The woven, substantially tubular nature of flexible member 130 provides several features that simultaneously contribute to the ability of fixation devices described herein to achieve their intended use(s): creep-resistance (or resistance to slacking of the individual contact points between interlacing strands of the weave over significant durations under relevant tension) and the transformable ability to provide lateral and torsional flexibility when flexible member 130 is not under tension and the different, transformed ability to provide sufficient functional torsional rigidity to efficiently and effectively transmit torque applied at the anchor portion side of flexible member 130 to the cap portion side of flexible member 130 when flexible member 130 is under sufficient axial tension. Example torques flexible member 130 would be expected to be able to effectively transfer may be 150 foot-pounds of torque.

First, how much a given material or composition of material will stretch out over time is at least partly a function of the tension each portion of that material or composition of material is subjected to, and how that compares with the tensile strength of the material. The woven nature of flexible member 130 more evenly distributes axial and torsional forces across the individual strands of the weave, allowing for lower peak tensions across the individual strands for a given amount of total tension or torque applied to flexible member 130. Forming strands of flexible member 130 of a material such as UHMWPE further provides an increased tensile strength and resistance to stretching to reduce or prevent flexible member 130 from creeping sufficiently that it loses its ability to functionally maintain sufficient axial and torsional tension and rigidity. However, any other suitable material composition for flexible member 130 is also contemplated.

Second, the woven nature of flexible member 130 and the coupled anchor and cap portions, having the above-described functionalities, work synergistically to provide the emergent properties the described fixation devices as a whole possess, but which are not possessed by any one of their components—specifically the above-described transformable and transformed abilities. For example, an ability of flexible member 130 to effectively transmit sufficient torque is at least partly a function of the ability to restrict relative motion between relatively proximate points of the flexible member 130. In embodiments described in this disclosure, these relatively proximate points may be considered points of contact between interlacing strands of the weave. When torque is applied across flexible membrane 130, that torque induces tensions in the individual strands of the weave. If unbalanced in any of the three spatial dimensions, these tensions will cause these points of contact between interlacing strands of a flexible material to slightly shift positions relative to neighboring points of contact. This shifting is the process of deformation which prevents effective transmission of torque through a flexible material. However, the woven nature of the individual strands of flexible member 130 provide additional restrictions in the degrees of freedom this slight shifting of those contact points between interlaced strands can take. This is especially true where strands cross and interlace with one another at sufficiently large acute angles (e.g., right angles) because each crossing strand has its strongest direction of pull aligned with the weakest direction of pull of the other strand. Accordingly, so long as flexible member 130 is held under sufficient tension to sufficiently prevent longitudinal shifting of contact points between interlaced strands, the woven nature also prevents rotational shifting of those contact points that would be induced by the torque.

Accordingly, since anchor portion 110, 610 is driven directly and advanced distally into bone while cap portion 120, 420, 520 is held longitudinally stationary against at least one of a bone plate (see, e.g., bone plate 900 in FIG. 9), other rigid body, or a bone of the patient, flexible member 130 being fixedly coupled therebetween causes the individual woven strands to act as buttresses to one another, resisting deformation of flexible member 130 as the anchor portion is advanced and as the cap portion is indirectly driven by the transferred torque.

The exemplary implementations, embodiments, and arrangements disclosed herein are based in part on the surprising advantages derived from having a flexible member having a fixed length, woven tubular design in conjunction with attachment of a first end of that flexible member to an anchor portion having a direct interface with a driver tool and attachment of a second end of that flexible member to a cap portion to which the fixation device transmits torque, such that torque is applied directly to the distal, anchor component and does not originate from the proximal, cap component.

Figure 9:
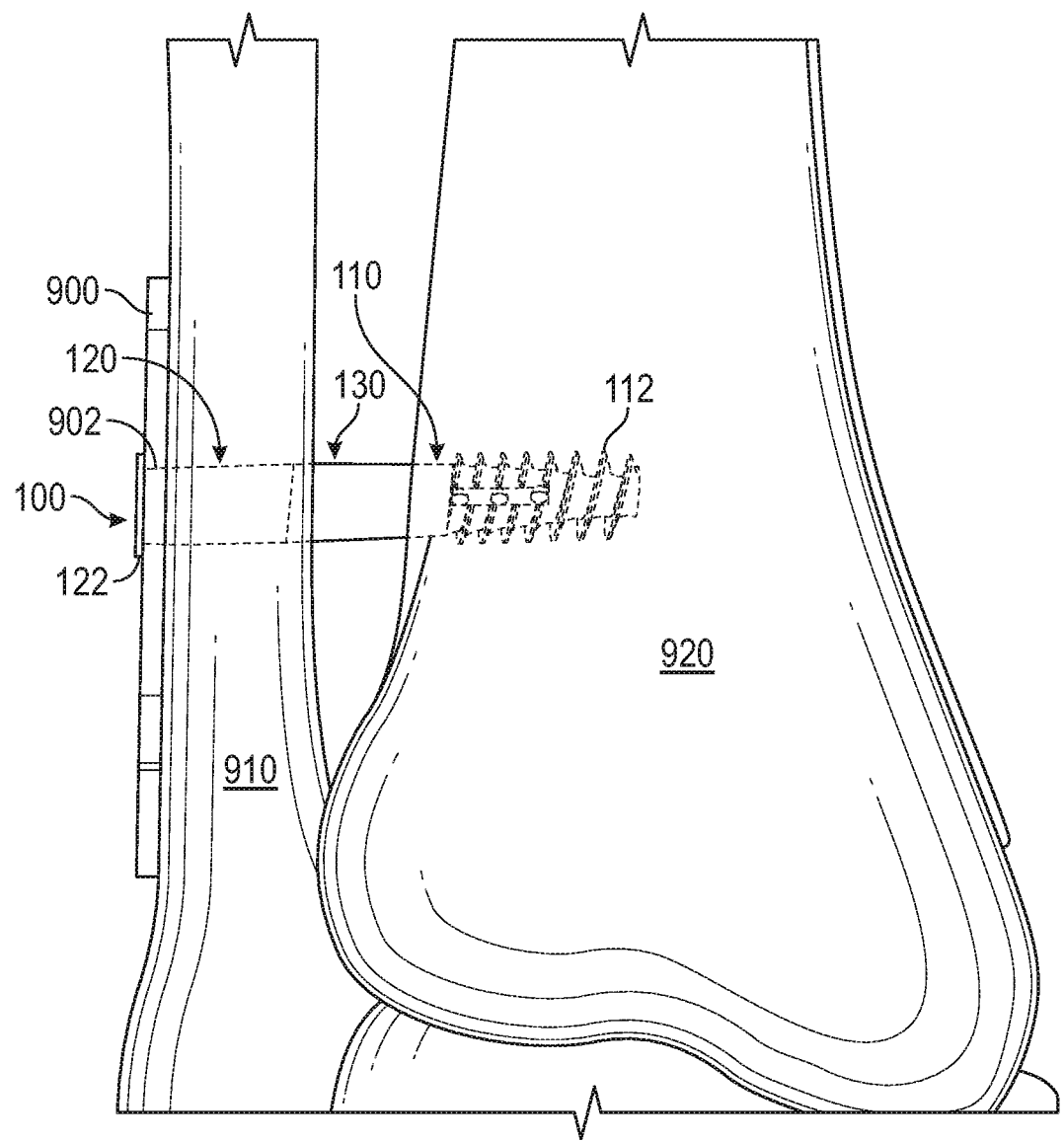
FIG. 9 illustrates a fixation device disposed at least partially within a tibia and a fibula of a patient, according to some embodiments.

FIG. 9 illustrates fixation device 110 disposed at least partially within a tibia 920 and a fibula 910 of a patient for syndesmotic repair, according to some embodiments. As shown, bone plate 900 is placed against the lateral side of the fibula and a pilot hole (not shown) may be drilled through fibula 910 and into tibia 920. At least a terminal end of a driving tool may then be inserted through aperture 124 of cap portion 120, through the hollow center of flexible portion 130, to interface in the complementary-shaped aperture 116 of anchor portion 110. Flexible portion 130 may be held in sufficient longitudinal or axial tension by pulling cap portion 120 away from anchor portion 110 as the distal tip of anchor portion 110 is inserted through aperture 902 of bone plate 900 and through the hole in fibula 910 in preparation of driving anchor portion 110 into tibia 920. As anchor portion 110 is directly driven to rotate by driver tool and extends distally into tibia 920, the fixed length of flexible membrane 130 goes taut and, as the longitudinal or axial tension builds in flexible membrane 130 so does its rigidity and torque is effectively transmitted through flexible membrane to rotate cap 120. This torque will be relatively small at first, a product of the initially lower longitudinal or axial tension and, also, a consequently lower frictional force between plate 900 and cap portion 120. However, longitudinal or axial tension increase rapidly, as does the torsional rigidity of flexible member 130, as anchor portion 110 distally advances and as a separation between anchor portion 110 and cap portion 120 reaches the fully extended, fixed length of flexible member 130. Once anchor portion 110 is driven sufficiently distally, fixation device 10 fixes fibula 910 in a suitable orientation with tibia 920. Driving tool can be withdrawn from aperture 124 of cap portion 120 and the initial incision closed. In this way, the bones of the lower leg are supported until the ligaments and other soft tissue can heal properly. An added advantage provided by fixation devices as disclosed herein is that the flexibility of the weave, while readily resisting torsional or twisting/bunching deformation when torque is applied, can still allow a very modest degree of freedom in the "skewing" or "leaning" deformation sense when that torque is no longer applied after implantation. For example, slight lateral (or radial in this case) displacements between the individual longitudinal axes of the cap and anchor portions are accommodated by flexible member 130. This also helps solve problems in current devices such as "suture sawing."

As stated above, the fixation devices described herein are well-suited for use in syndesmotic repair. However, the device can also be used in other soft tissue fixation/augmentation orthopedic procedures. In still another aspect, the device can be used in the fixation/fusion of osteotomies or fractures to aid in a boney fusion.

Embodiments of the fixation devices described herein may passes through two, three or four cortices. Where the fixation device is utilized to stabilize a fracture in, for example, the tibia, passing through or nearly through the tibia only, the fixation device passes through two cortices. Where the fixation device passes completely through the fibula and into the tibia (see, e.g., FIG. 9), the fixation device passes through three—two of the fibula and one the tibia. Where the fixation device passes completely through both the fibula and the tibia (or nearly through the tibia), the fixation device passes through four—two of the fibula and two of the tibia.

Moreover, in the case of syndesmosis repair, fixation devices described herein address the issue of the distal nerve impingement common with current solutions. For example, some current solutions use a button and lace system in which a metal strand is anchored to the tibia and looped and pulled through several passes through the fibula and between the tibia and this button. When these laces are cinched up, local nerves are pinched and cause permanent damage. Moreover, the fixed length of flexible member 130 ensures proper tension is reached during implantation, so the practitioner does not have to perform a secondary tensioning operation.

Figure 10:
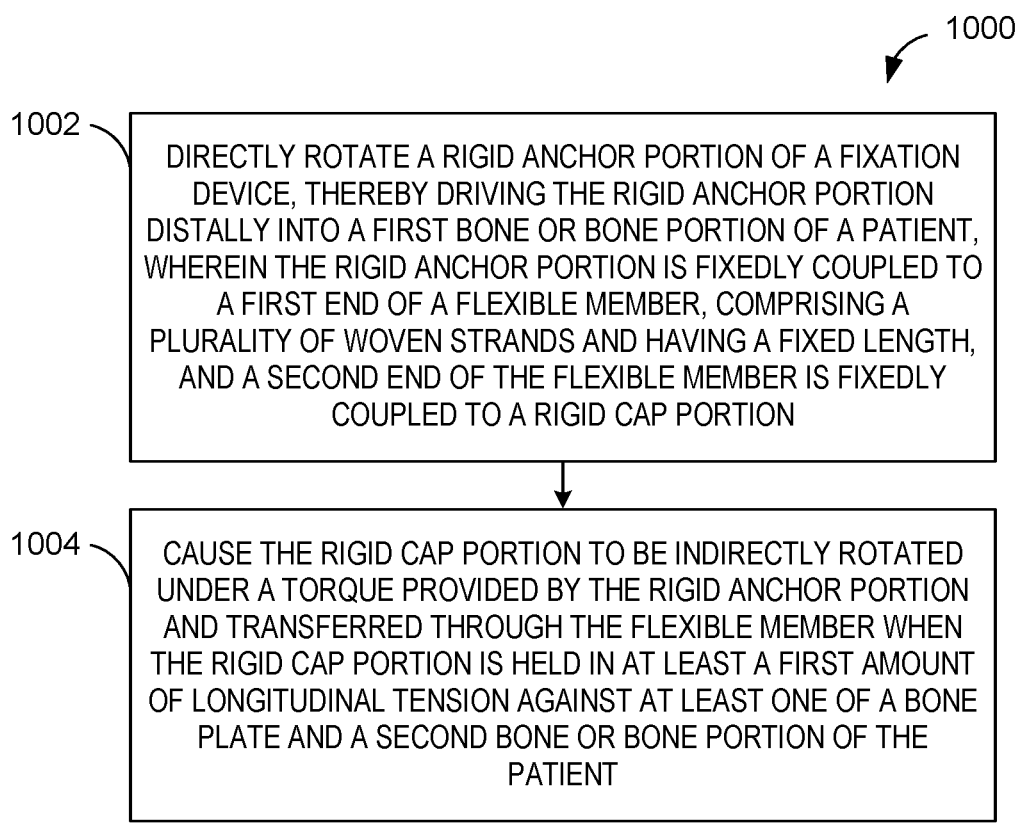
FIG. 10 illustrates a flowchart related to a method of using a fixation device, according to some example embodiments.

FIG. 10 illustrates a flowchart 1000 related to a method of using a fixation device, according to some example embodiments. Applicable fixation devices include but are not limited to any fixation device as shown, described and/or inferred herein. While certain actions and/or steps are discussed in a particular order, the present disclosure is not so limited and, unless specifically indicated, a method of using a fixation device as discussed anywhere in this disclosure may include one or more additional steps and/or actions, omit one or more disclosed steps and/or actions, or comprise any combination of such steps and/or actions in any suitable order.

Flowchart includes block 1002, which includes directly rotating a rigid anchor portion of a fixation device, thereby driving the rigid anchor portion distally into a first bone or bone portion of a patient, wherein the rigid anchor portion is fixedly coupled to a first end of a flexible member, comprising a plurality of woven strands and having a fixed length, and a second end of the flexible member is fixedly coupled to a rigid cap portion. For example, anchor portion 110, 610 of fixation device 100, 600 is configured to be directly rotated by a driving tool as described and/or inferred anywhere in this disclosure, thereby driving anchor portion 110, 610 distally into a first bone or bone portion of a patient (e.g., tibia 920 of FIG. 9). As described throughout this disclosure, anchor portion 110, 610 is fixedly coupled to a first end of flexible member 130, which includes a plurality of woven strands (e.g., 132a-b, 134a-b) and having a fixed length $L_2$, and a second end of flexible member 130 is fixedly coupled to cap portion 120, 420, 520.

Flowchart includes block 1004, which includes causing the rigid cap portion to be indirectly rotated under a torque provided by the rigid anchor portion and transferred through the flexible member when the rigid cap portion is held in at least a first amount of longitudinal tension against at least one of a bone plate and a second bone or bone portion of the patient. For example, a practician implanting the technology may use the driving tool to directly rotate anchor portion 110, 610, through aperture 124 in cap portion 120, 420, 520 and through the hollow center of flexible member 1130, which causes cap portion 120, 420, 520 to be indirectly rotated under a torque provided by anchor portion 110, 610 and transferred through flexible member 130 when cap portion 120, 420, 520 is held in at least a first amount of longitudinal tension against at least one of bone plate 900 and a second bone or bone portion of the patient (e.g., fibula 910 in FIG. 9).

Such a method of use may include any other suitable step or action for implanting any fixation device described in or inferred by this disclosure and/or using such a fixation device once implanted.

Figure 11:
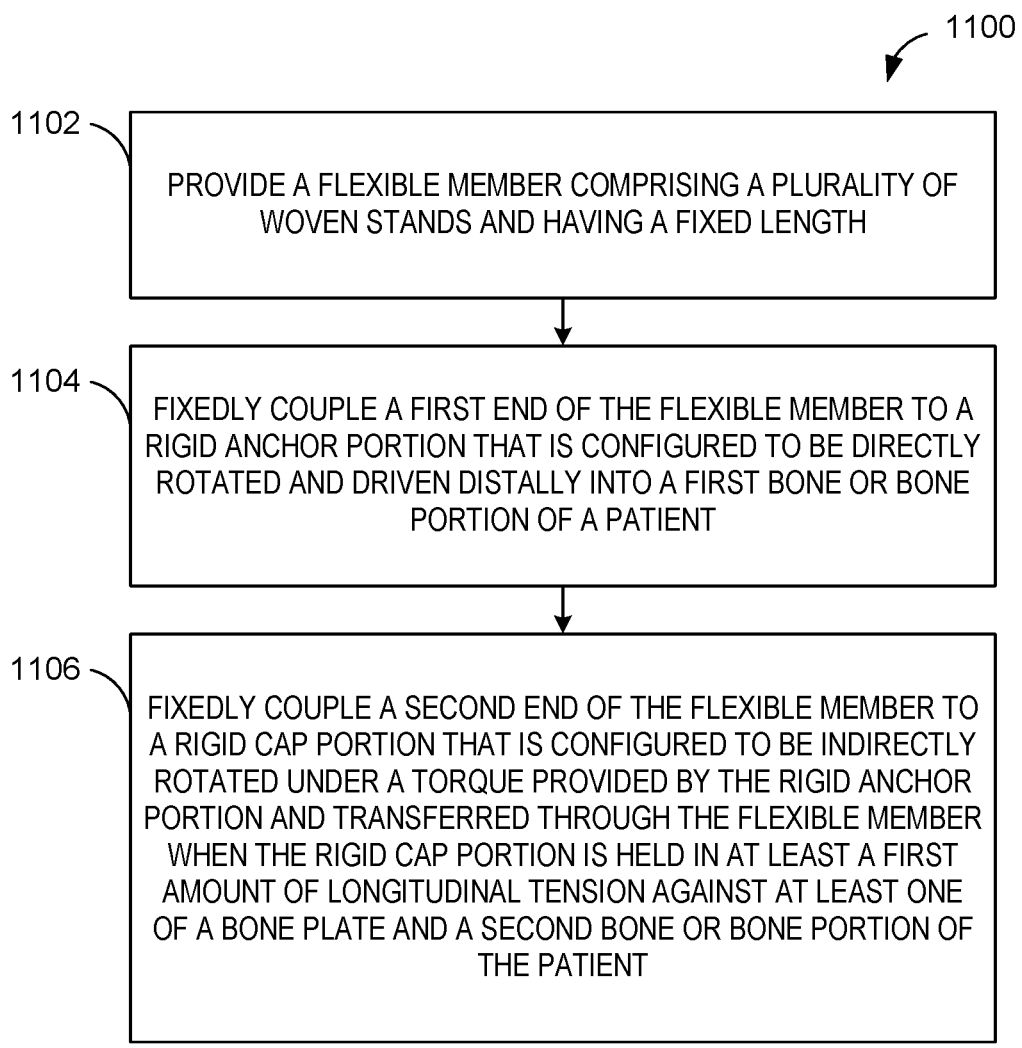
FIG. 11 illustrates a flowchart related to a method of manufacturing a fixation device, according to some example embodiments.

FIG. 11 illustrates a flowchart related to a method of manufacturing a fixation device, according to some example embodiments. Applicable fixation devices include but are not limited to any fixation device as shown, described and/or inferred in this disclosure. While certain actions and/or steps are discussed in a particular order, the present disclosure is not so limited and, unless specifically indicated, a method of manufacturing a fixation device as discussed anywhere in this disclosure may include one or more additional steps and/or actions, omit one or more disclosed steps and/or actions, or comprise any combination of such steps and/or actions in any suitable order.

Flowchart includes block 1102, which includes providing a flexible member comprising a plurality of woven stands and having a fixed length. For example, flexible member 130 may be provided, including a plurality of woven stands (e.g., 132a-b, 134a-b), flexible member 130 having a fixed length $L_2$, as previously described. In some embodiments, providing the flexible member having the fixed length may include weaving the plurality of stands (e.g., 132a-b, 134a,b) such that a first subset of the strands passing in a first relative direction are interlaced with a second subset of the strands passing in a second relative direction that is substantially different than the first relative direction (e.g., 90°).

Flowchart includes block 1104, which includes fixedly coupling a first end of the flexible member to a rigid anchor portion that is configured to be directly rotated and driven distally into a first bone or bone portion of a patient. For example, a first end of flexible member 130 may be fixedly coupled to anchor portion 111, 611, which is configured to be directly rotated and driven distally into a first bone or bone portion of a patient (e.g., tibia 920 in FIG. 9), as described anywhere in this disclosure.

Flowchart includes block 1106, which includes fixedly coupling a second end of the flexible member to a rigid cap portion that is configured to be indirectly rotated under a torque provided by the rigid anchor portion and transferred through the flexible member when the rigid cap portion is held in at least a first amount of longitudinal tension against at least one of a bone plate and a second bone or bone portion of the patient. For example, a second end of flexible member 130 may be fixedly coupled to cap portion 120, 420, 520, which is configured to be indirectly rotated under a torque provided by anchor portion 110, 610 and transferred through flexible member 130 when cap portion 110, 610 is held in at least a first amount of longitudinal tension against at least one of bone plate 900 and a second bone or bone portion of the patient (e.g., fibula 910 of FIG. 9).

Such a method of manufacture may include any other step of providing, fabricating, manufacturing, coupling, fixing or any other suitable action for manufacturing any feature or component of any fixation device described in or inferred by this disclosure.

General Interpretive Principles for the Present Disclosure

Various aspects of the novel systems, apparatuses, and methods are described more fully hereinafter with reference to the accompanying drawings. The teachings disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the novel systems, apparatuses, and methods disclosed herein, whether implemented independently of or combined with any other aspect of the disclosure. For example, a system or an apparatus may be implemented, or a method may be practiced using any one or more of the aspects set forth herein. In addition, the scope of the disclosure is intended to cover such a system, apparatus or method which is practiced using other structure, functionality, or structure and functionality in addition to or other than the various aspects of the disclosure set forth herein. It should be understood that any aspect disclosed herein may be set forth in one or more elements of a claim. Although some benefits and advantages of the preferred aspects are mentioned, the scope of the disclosure is not intended to be limited to particular benefits, uses, or objectives. The detailed description and drawings are merely illustrative of the disclosure rather than limiting, the scope of the disclosure being defined by the appended claims and equivalents thereof.

With respect to the use of plural vs. singular terms herein, those having skill in the art can translate from the plural to the singular and/or from the singular to the plural as is appropriate to the context and/or application. The various singular/plural permutations may be expressly set forth herein for sake of clarity.

When describing an absolute value of a characteristic or property of a thing or act described herein, the terms "substantial," "substantially," "essentially," "approximately," and/or other terms or phrases of degree may be used without the specific recitation of a numerical range. When applied to a characteristic or property of a thing or act described herein, these terms refer to a range of the characteristic or property that is consistent with providing a desired function associated with that characteristic or property.

In those cases where a single numerical value is given for a characteristic or property, it is intended to be interpreted as at least covering deviations of that value within one significant digit of the numerical value given.

If a numerical value or range of numerical values is provided to define a characteristic or property of a thing or act described herein, whether or not the value or range is qualified with a term of degree, a specific method of measuring the characteristic or property may be defined herein as well. In the event no specific method of measuring the characteristic or property is defined herein, and there are different generally accepted methods of measurement for the characteristic or property, then the measurement method should be interpreted as the method of measurement that would most likely be adopted by one of ordinary skill in the art given the description and context of the characteristic or property. In the further event there is more than one method of measurement that is equally likely to be adopted by one of ordinary skill in the art to measure the characteristic or property, the value or range of values should be interpreted as being met regardless of which method of measurement is chosen.

It will be understood by those within the art that terms used herein, and especially in the appended claims (e.g., bodies of the appended claims) are intended as "open" terms unless specifically indicated otherwise (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

In those instances where a convention analogous to "at least one of A, B, and C" is used, such a construction would include systems that have A alone, B alone, C alone, A and B together without C, A and C together without B, B and C together without A, as well as A, B, and C together. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include A without B, B without A, as well as A and B together."

Various modifications to the implementations described in this disclosure can be readily apparent to those skilled in the art, and generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "exemplary" is used exclusively herein to mean "serving as an example, instance, or illustration." Any implementation described herein as "exemplary" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

What is claimed is:

1. A semi-rigid fixation device for orthopedic fixation, comprising:
    a rigid anchor portion configured to be directly rotated and driven distally into a first bone or bone portion of a patient; wherein a proximal end of the rigid anchor portion comprises an aperture configured to receive a tool configured to impart a torque directly to the rigid anchor portion;
    a rigid cap portion configured to be held in tension against at least one of a bone plate and a second bone or bone portion of the patient and indirectly rotated under a torque provided by the rigid anchor portion; and
    a flexible member comprising a plurality of woven stands, wherein:
        the flexible member has a fixed length between a first end and a second end,
        the first end is fixedly coupled to the rigid anchor portion, and
        the second end is fixedly coupled to the rigid cap portion such that a torque provided by the direct rotation of the rigid anchor portion is transferred through the flexible member to the rigid cap when the flexible member is held in at least a first amount of longitudinal tension;
    wherein a side of the rigid anchor portion comprises at least one hole bored into the aperture in the proximal end of the rigid anchor portion, the first end of the flexible member tied or otherwise fixed to the rigid anchor portion through the at least one hole.

2. The fixation device of claim 1, wherein the rigid anchor portion is fixedly coupled to the first end via a first press-fit connection and the rigid cap portion is fixedly coupled to the second end via a second press-fit connection.

3. The fixation device of claim 1, wherein at least one of the rigid anchor portion and the rigid cap portion is substantially cylindrical.

4. The fixation device of claim 1, wherein the rigid anchor portion, the rigid cap portion and the flexible member are coupled in-line such that a longitudinal axis of extension through a center of the fixation device is coincident with individual longitudinal axes through respective centers of the rigid anchor portion, the rigid cap portion and the flexible member.

5. The fixation device of claim 1, wherein at least one of the rigid anchor portion and the rigid cap portion comprises one or more of Ti-6Al-4V, PEEK, polyester, polyamide, polyurethane, polyethylene, ultra-high molecular weight polyethylene (UHMWPE).

6. The fixation device of claim 1, wherein the rigid anchor portion comprises threads configured to bite into the first bone or bone portion of the patient when the rigid anchor portion is directly rotated.

7. The fixation device of claim 6, wherein driving the rigid anchor portion distally into the first bone or bone portion simultaneously increases the longitudinal tension in the flexible member.

8. The fixation device of claim 1, wherein the rigid cap portion comprises an aperture and the flexible member comprises a hollow center, each configured to receive at least a terminal portion of the tool therethrough.

9. The fixation device of claim 8, wherein a shape of at least a distal portion of the rigid anchor portion aperture may be complementary to a shape of a terminal end of the tool, thereby allowing the tool to directly releasably engage with the rigid anchor portion through the aperture in the rigid cap portion and through the hollow center of the flexible member.

10. The fixation device of claim 1, wherein a proximal end of the rigid cap portion comprises a rim.

11. The fixation device of claim 10, wherein at least a portion of a distal surface of the rim is configured to be in direct contact with the at least one of the bone plate and the second bone or bone portion of the patient as the rigid anchor portion is driven distally into the first bone or bone portion of the patient.

12. The fixation device of claim 7, wherein the flexible member transmits the torque to the rigid cap portion simultaneous to, and at least partially as a result of, the longitudinal tension in the flexible member reaching or exceeding the first amount, thereby causing the rigid cap portion to rotate through a substantially same angle as the rigid anchor portion.

13. The fixation device of claim 1, wherein the rigid cap portion comprises a locking feature configured to releasably engage with the at least one of the bone plate and the second bone or bone portion of the patient.

14. The fixation device of claim 1, wherein the rigid cap portion comprises threads configured to engage with at least one of the bone plate and the second bone or bone portion of the patient.

15. The fixation device of claim 1, wherein the rigid cap portion comprises one or more circumferential blades configured to provide a friction-fit seating of the rigid cap portion in at least one of an aperture of the bone plate and the second bone or bone portion of the patient.

16. The fixation device of claim 1, wherein the rigid anchor portion comprises one or more circumferential blades configured to provide a friction-fit seating of the rigid anchor portion in the first bone or bone portion of the patient.

17. The fixation device of claim 1, wherein the plurality of woven strands form a substantially cylindrical tube.

18. The fixation device of claim 1, wherein the plurality of woven strands comprises a first subset of strands passing in a first relative direction interlaced with a second subset of strands passing in a second relative direction that is substantially different than the first relative direction.

19. The fixation device of claim 18, wherein the first relative direction is substantially perpendicular to the second relative direction.

20. The fixation device of claim 18, wherein the first subset of strands buttress the second set of strands and the second set of strands buttress the first set of strands, thereby resisting deformation of the flexible member as the rigid anchor portion is directly rotated and driven distally into the first bone or bone portion and as the rigid cap portion is indirectly rotated under the torque provided by the rigid anchor portion.

21. The fixation device of claim 1, wherein the plurality of woven strands comprise ultra-high molecular weight polyethylene.

22. The fixation device of claim 1, wherein the woven pattern of the plurality of woven strands extends the entire fixed length between the first and second ends of the flexible member, at least one of the first and second ends of the flexible member being fixedly tied, melted or potted to the respective rigid anchor portion or rigid cap portion.

23. The fixation device of claim 1, wherein the woven pattern of the plurality of woven stands transitions to a sutured pattern at the first and second ends of the flexible member, at least one of the first and second ends of the flexible member being fixedly tied, melted or potted to the respective rigid anchor portion or rigid cap portion.

* * * * *